United States Patent
Bonrath et al.

(10) Patent No.: US 7,153,994 B2
(45) Date of Patent: Dec. 26, 2006

(54) MANUFACTURE OF TRIMETHYLHYDROQUINONE DIACYLATES

(75) Inventors: Werner Bonrath, Freiburg (DE); Michael Schneider, Frick (CH)

(73) Assignee: DSM IP Assets B.V., TE Heerlen (NL)

( * ) Notice: Subject to any disclaimer, the term of this patent is extended or adjusted under 35 U.S.C. 154(b) by 392 days.

(21) Appl. No.: 10/498,626

(22) PCT Filed: Dec. 7, 2002

(86) PCT No.: PCT/EP02/13890

§ 371 (c)(1),
(2), (4) Date: Jun. 11, 2004

(87) PCT Pub. No.: WO03/051812

PCT Pub. Date: Jun. 26, 2003

(65) Prior Publication Data

US 2005/0038286 A1    Feb. 17, 2005

(30) Foreign Application Priority Data

Dec. 14, 2001  (EP) ................................. 01129794

(51) Int. Cl.
*C07C 69/00* (2006.01)
(52) U.S. Cl. ....................................... 560/144
(58) Field of Classification Search ................ 560/144
See application file for complete search history.

(56) References Cited

U.S. PATENT DOCUMENTS

| T900,015 I4 | 7/1972 | Thweatt et al. |
|---|---|---|
| 6,417,409 B1 | 7/2002 | Krill et al. |

FOREIGN PATENT DOCUMENTS

| DE | 2 149 159 | 4/1972 |
|---|---|---|
| EP | 0 916 642 | 5/1999 |
| EP | 1 028 103 A1 | 8/2000 |
| EP | 1 134 218 | 9/2001 |
| EP | 1 180 517 | 2/2002 |
| WO | WO 98/21197 | 5/1998 |

OTHER PUBLICATIONS

Derwent English abstract of DE 2 149 159.

*Primary Examiner*—Joseph K. McKane
*Assistant Examiner*—Robert Shiao
(74) *Attorney, Agent, or Firm*—Bryan Cave LLP

(57) ABSTRACT

A process for the manufacture of 2,3,5-trimethylhydroquinone diacylate comprising reacting ketoisophorone with an acylating agent in the presence of a NH- or CH-acidic catalyst, particularly certain bis(perfluorinated hydrocarbyl sulphonyl) imides and metal salts thereof and, respectively, certain tris(perfluoroalkanesulphonyl or pentafluorobenzenesulphonyl) methanes and metal salts thereof. The acylating agent is particularly an acid anhydride, an acyl halide or an enol ester. The so-obtained 2,3,5-trimethylhydroquinone diacylate can be converted into (all-rac)-α-tocopherol by transesterification to yield 2,3,5-trimethylhydroquinone and reaction of the latter with isophytol. (all-rac)-α-Tocopherol itself is the most active member of the vitamin E group.

20 Claims, No Drawings

MANUFACTURE OF TRIMETHYLHYDROQUINONE DIACYLATES

This application is the National Stage of International Application No. PCT/EP02/13890, filed Dec. 7, 2002.

The present invention is concerned with a process for the manufacture of 2,3,5-trimethylhydroquinone diacylates by reacting ketoisophorone with an acylating agent in the presence of a so-called NH- or CH-acidic catalyst. The products of the process are useful as reactants for the manufacture of 2,3,5-trimethylhydroquinone, itself a known valuable reactant for the manufacture of (all-rac)-α-tocopherol, the most active member of the vitamin E group.

2,3,5-Trimethylhydroquinone diacylates are known to be producible by reacting ketoisophorone with an acylating agent in the presence of a strongly acidic catalyst. Many such catalysts have been proposed in the past for this purpose, in particular protonic acids, e.g. such inorganic acids as sulphuric acid; such organic acids as p-toluenesulphonic acid; strongly acidic ion exchange resins; and such Lewis acids as zinc chloride, boron trifluoride, antimony pentafluoride and titanium tetrachloride: see inter alia German Offenlegungsschrift 2149159 and European Patent Publications EP 0916642 A1 and EP 1028103 A1. In accordance with the present invention it has been found that the conversion of ketoisophorone to 2,3,5-trimethylhydroquinone diacylates can be advantageously accomplished by the use of NH-acidic or CH-acidic catalysts, especially those which have been found to be useful catalysts for the condensation of 2,3,5-trimethylhydroquinone with isophytol to yield α-tocopherol, as described in PCT Publication WO 98/21197 and European Patent Publications EP 1180517 A1 and EP 1134218 A1. Advantages of such catalysts used in the process in accordance with the present invention are the avoidance of corrosion, the avoidance of waste water contamination with heavy metal ions and the high selectivity.

Accordingly, the present invention provides a process for the manufacture of a 2,3,5-trimethylhydroquinone diacylate, which process comprises reacting ketoisophorone with an acylating agent in the presence of a NH-acidic catalyst, especially one of the general formula $$[(R^1SO_2)_2N]_xR^2 \quad (I)$$

or a CH-acidic catalyst, especially one of the general formula $$[(R^3SO_2)_3C]_xR^2 \quad (II)$$

wherein each of $R^1$, independently, signifies a perfluoroalkyl group $C_nF_{2n+1}$ or pentafluorophenyl, or both symbols $R^1$ together signify a poly-difluoromethylene group $-(CF_2)_m-$, $R^2$ signifies a proton or a metal cation selected from the group consisting of boron, magnesium, aluminium, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum and gold cations, each of $R^3$, independently, signifies a perfluoroalkyl group $C_nF_{2n+1}$ or pentafluorophenyl, m signifies an integer from 2 to 4, n signifies an integer from 1 to 10 and x signifies an integer from 1 to 5 corresponding to the valency of the proton (1) or the metal cation (1, 2, 3, 4 or 5) signified by $R^2$.

Examples of the cations signified by $R^2$ in both formulae above, using their chemical symbols, are $B^{3+}$, $Mg^{2+}$, $Al^{3+}$, $Si^{4+}$, $Sc^{3+}$, $Ti^{4+}$, $V^{3+}$, $V^{3+}$, $Mn^{2+}$, $Mn^{4+}$, $Fe^{2+}$, $Fe^{3+}$, $Co^{2+}$, $Ni^{2+}$, $Cu^+$, $Cu^{2+}$, $Zn^{2+}$, $Y^{3+}$, $Zr^{4+}$, $Rh^{3+}$, $Pd^{2+}$, $Ag^+$, $Sn^{4+}$, $La^{3+}$, $Ce^{3+}$, $Pr^{3+}$, $Nd^{3+}$, $Eu^{2+}$, $Dy^{3+}$, $Tm^{3+}$, $Yb^{3+}$, $Hf^{4+}$, $Pt^{2+}$ and $Au^{3+}$.

Not only some of the above-defined NH-acidic catalysts of the formula I wherein $R^2$ signifies a proton [all being bis(perfluorinated hydrocarbyl sulphonyl)imides] but also some of their metal salts amongst the catalysts of formula I are known compounds. Those catalysts of formula I which may still not be known can be produced by methods analogous to the published methods for producing bis(trifluoromethylsulphonyl)imide and its metal salts and the higher members of these sulphonimides and their metal salts: see, for example, EP 364340/U.S. Pat. No. 5,256,821, Japanese Patent Publications (Kokai) 246338/1995, 064238/1996 (with the US counterpart U.S. Pat. No. 5,650,244), 057110/1997, 169690/1997, 176063/1997, 176171/1997, 241184/1997, 230166/1998, 330314/1998 and 209338/1999, DOS 4217366/U.S. Pat. No. 5,502,251, DOS 19533711/U.S. Pat. No. 5,723,664, Chemiker Zeitung 96, 582–583 (1972), Chem. Lett. 1995, 307–308, Synlett 1996, 171–172, 265–266 and 839–841, Inorg. Chem. 35(7), 1918–1925 (1996), J. Power Sources 68, 307–310 (1997) and Cat. Today 36(1), 81–84 (1997) as well as the further literature references mentioned in this state of the art. For example, many of the salts can be produced from the appropriate bis(perfluorinated hydrocarbyl sulphonyl)imide of formula I in which $R^2$ signifies a proton and the metal acetate, oxide, hydroxide or alcoholate featuring the desired metal cation. In the case of the aluminium, zinc and various other metal salts these can also be produced using the corresponding alkylmetal or dialkylmetal hydride, e.g. diethylzinc or triethylaluminium or, respectively, diisobutylaluminium hydride.

In some cases the metal salts can be present in monomeric or polymeric form and, accordingly, formula I is intended to embrace all such forms. Further, these catalysts can be used in isolated form or produced in situ.

Examples of a catalyst of formula I in which the symbols $R^1$ together signify a poly-difluoromethylene group $-(CF_2)_m-$ are 4,4,5,5,6,6-hexafluoro-(1,3,2)dithiazinane-1,3-dioxide and its silver salt.

Some of the CH-acidic catalysts of the formula II wherein $R^2$ signifies a proton and their metal salts are known compounds. Thus in Inorg. Chem. 27, 2135–2137 (1988) K. Seppelt and L. Turowsky describe for the first time the preparation of tris(trifluoromethanesulphonyl)methane, $(CF_3SO_2)_3CH$, and of four salts thereof, viz. the potassium, rubidium, silver and cesium salts. The lithium and further metal salts of $(CF_3SO_2)_3CH$ and other tris(perfluoroalkanesulphonyl)methides and their preparation are described in U.S. Pat. No. 5,273,840. Also developing the original work of Seppelt and Turowsky, F. J. Waller et al. describe in J. Org. Chem. 64, 2910–2913 (1999) the further preparation of $(CF_3SO_2)_3CH$ and its cesium salt, and also the preparation of the corresponding scandium and ytterbium salts. In Synlett 1999, No. 12, 1990–1992, J. Nishikido et al. describe the preparation of scandium, yttrium and, in general, lanthanide (III) tris(perfluorobutanesulphonyl)methide complexes. Further literature concerning the preparation of these and further metal tris(perfluoroalkanesulphonyl)methides includes U.S. Pat. No. 5,554,664 and the many references mentioned in this and in other aforementioned publications.

The tris(perfluoroalkanesulphonyl or pentafluorobenzenesulphonyl)methanes or metal salts thereof embraced by the formula II hereinbefore and used as the catalysts in the process of the present invention can be produced according to such published methods or, in the case of those methanes or metal salts thereof which may still not be known, according to analogous methods.

Preferred NH- and CH-acidic catalysts for use in the process of the present invention are those NH-acidic catalysts of the formula I wherein each of $R^1$ signifies trifluoromethyl or pentafluoroethyl, or both symbols $R^1$ together signify perfluoro-1,3-propylene, especially those wherein in addition $R^2$ signifies a proton; and those CH-acidic catalysts of the formula II wherein each of $R^3$ signifies trifluoromethyl, especially those wherein in addition $R^2$ signifies a proton or a divalent nickel cation.

The acylating agent used in the process of the present invention may be any acylating agent that is conventionally used in the conversion of ketoisophorone to 2,3,5-trimethylhydroquinone acylates, particularly acid anhydrides, acyl halides, and enol esters. Examples of acid anhydrides are straight or branched chain alkanoic acid anhydrides such as acetic, propionic and butyric anhydride. Examples of acyl halides are straight or branched chain alkanoyl chlorides such as acetyl, propionyl and butyryl chloride. Finally, examples of enol esters are isopropenyl acetate and butyrate. The preferred acylating agent is acetic anhydride or acetyl chloride, especially acetic anhydride.

The process of the present invention can be carried out in the presence or in the absence of a solvent. As a solvent, any inert polar or non-polar organic solvent or any mixture of two or more of such solvents can be used. Suitable classes of polar organic solvents include aliphatic and cyclic ketones, e.g. diethyl ketone and isobutyl methyl ketone and, respectively, cyclopentanone and isophorone; and aliphatic and cyclic esters, e.g. ethyl acetate and isopropyl acetate, and, respectively, γ-butyrolactone, ethylene carbonate and propylene carbonate. As suitable classes of non-polar organic solvents there may be mentioned aliphatic hydrocarbons, e.g. hexane, heptane and octane, and aromatic hydrocarbons, e.g. benzene, toluene and the xylenes. The reaction can be effected in a single solvent phase, e.g. in toluene alone as the solvent, or in a biphasic solvent system, e.g. in ethylene or propylene carbonate and heptane.

While the ratio of acylating agent to ketoisophorone is not narrowly critical the ratio of acylating agent (equivalents) to ketoisophorone (moles) is suitably from about 1:1 to about 5:1, preferably from about 2:1 to about 3:1, and is most preferably about 3:1.

The amount of catalyst of formula I or II used is suitably about 0.1 to about 2.0 mole %, preferably about 0.5 to about 1.5 mole %, and most preferably about 0.8 to about 1.2 mole %, based on the moles of ketoisophorone present.

The process is conveniently carried out at temperatures from about 20° C. to about 60° C., preferably from about 30° C. to about 50° C.

Moreover, the process is conveniently carried out under an inert gas atmosphere, preferably under gaseous nitrogen or argon.

The progress of the reaction is suitably monitored by gas chromatography and mass spectrometry of samples taken from the reaction mixture at various time intervals during the reaction.

The produced 2,3,5-trimethylhydroquinone diacylate can be isolated after distilling off the remaining acylating agent and the secondary product formed in the acylation, e.g. acetic acid when acetic anhydride is used as the acylating agent, by extraction of the crude product mixture with a suitable organic solvent, e.g. toluene. For instance, in effecting this procedure using acetic anhydride as the acylating agent 2,3,5-trimethylhydroquinone diacetate was obtained as colourless crystals after evaporating off the toluene used as the extracting solvent. Another isolation procedure is the crystallization of the 2,3,5-trimethylhydroquinone diacylate from the mixture at the termination of the reaction by cooling, and, optionally, adding water, to the mixture to promote the crystallization.

The catalyst can be recovered by extraction with water or acid-water and concentration of the extract. Alternatively, the catalyst can be recovered by adding a biphasic solvent system, e.g. a carbonate (particularly ethylene carbonate or propylene carbonate) and an aliphatic hydrocarbon (particularly heptane or octane), and isolating it from the polar (carbonate) phase The 2,3,5-trimethylhydroquinone diacylate obtained by the process of the present invention can be converted into 2,3,5-trimethylhydroquinone by transesterification, i.e. by treatment with an alcohol, e.g. an aliphatic alcohol such as isopropanol or n-butanol. Depending on the amounts of alcohol and catalyst and on the temperature in the reaction mixture, the transesterification yields the unesterified 2,3,5-trimethylhydroquinone and the ester formed as the further product. The former product can be converted into (all-rac)-α-tocopherol by reaction with isophytol, preferably in a biphasic solvent system, e.g. in a solvent system comprising a polar solvent such as ethylene or propylene carbonate, and an non-polar solvent, particularly an aliphatic hydrocarbon such as heptane.

The invention is illustrated by the following Examples.

EXAMPLE 1

To a mixture of 20.28 g (199 mmol) of acetic anhydride and 218.4 mg (0.777 mmol) of bis(trifluoromethanesulphonyl)amine there were added, with stirring, 10.17 g (66.82 mmol) of ketoisophorone within 30 minutes under a nitrogen flow. After 20 minutes, the temperature rose from about 25° C. to about 46° C. The reaction mixture was then held at the higher temperature and the reaction allowed to proceed with stirring for an additional 2.5 hours. The reaction mixture was found to contain 88% of 2,3,5-trimethylhydroquinone diacetate (percentage given as area % according to gas chromatography) and minor amounts of unreacted ketoisophorone. The so-obtained product could be worked up by crystallization at about 4° C., e.g. from hexane, or by distillation.

EXAMPLE 2

The acylation reaction was carried out substantially as described in Example 1. After a reaction time of 3 hours, 3.88 g (about 4.9 ml; 66.88 mmol) of isopropanol were added under continuous stirring and nitrogen flow in order to quench the reaction by conversion of the remaining acetic anhydride into acetic acid and isopropyl acetate. The mixture was heated to 90° C. and after 8 hours was concentrated by distillation. 2,3,5-Trimethylhydroquinone diacetate was isolated from the mixture by crystallization at room temperature and filtration.

EXAMPLE 3

The acylation reaction was carried out substantially as described in Example 1. After completion of the acylation the remaining acetic anhydride was removed at 75° C./20 mbar (2 kPa). Then, 25 ml of toluene were added twice and removed by evaporation after each addition. The residue was dried at 60° C./30 mbar (3 kPa). To the so-obtained residue containing 15.11 g of crude 2,3,5-trimethylhydroquinone diacetate were added 78.48 g (0.8912 mmol) of ethylene carbonate under a nitrogen atmosphere, and the mixture was heated to 90° C. Then 3.88 g (about 4.9 ml; 66.88 mmol) of isopropanol were added to the mixture for the same purpose as in the case of Example 2 above. After 5 hours the reaction mixture was concentrated by distillation and 2,3,5-trimethylhydroquinone diacetate crystallized out at room temperature and could be removed from the mixture by filtration. The mother liquor containing the catalyst was recycled.

EXAMPLE 4

The acylation reaction was carried out substantially as described in Example 1. After completion of the acylation the remaining acetic anhydride was removed at 75° C./20 mbar (2 kPa). Then, 25 ml of toluene were added twice and removed by evaporation after each addition. The residue was dried at 60° C./30 mbar (3 kPa). To the so-obtained residue containing 15.2 g of crude 2,3,5-trimethylhydroquinone diacetate (90% content), there were added 78.48 g (0.8912 mmol) of ethylene carbonate under a nitrogen atmosphere. This mixture was heated to 100° C. and 37.31 g (270 mmol) of isopropanol were then added. After 5 hours reaction time 120 ml of heptane were added in one quantity, followed by 58 mmol isophytol during 30 minutes, the temperature of the reaction mixture being retained at 100° C. To isolate the resulting crude (all-rac)-α-tocopherol the solvent was evaporated under reduced pressure; this yielded 22.9 g of (all-rac)-α-tocopherol.

This Example illustrates a multistep process starting from ketoisophorone and the acylating agent acetic anhydride via the diacetate of 2,3,5-trimethylhydroquinone (not isolated) followed by the transesterfication with isopropanol to the unesterified 2,3,5-trimethylhydroquinone and finally involving the reaction of the last-named product with isophytol to afford (all-rac)-α-tocopherol. The excess amount of isopropanol used serves to saponify the formed 2,3,5-trimethylhydroquinone diacetate and to esterify the acetic anhydride, the ratio of isopropanol equivalents used being approximately 3:1 for these two purposes.

EXAMPLE 5

In analogy to Example 1, acylation/rearrangement reactions were carried out using various catalyst and/or other reactions conditions. The results are given in the Table below.

| Catalyst | Amount of catalyst | Reaction temperature | Reaction time | KIP GC-area % | TMHQ-DA GC-area % |
|---|---|---|---|---|---|
| $(CF_3SO_2)_2NH$ | 1.1 mole % | 45° C.* | 18 h | 6.5 | 82.7 |
| $(CF_3SO_2)_2NH$ | 1.1 mole % | 45° C. | 14 h | 1.2 | 88.0 |
| $(CF_3SO_2)_2NH$ | 2.2 mole % | 45° C. | 5 h | 0.2 | 88.5 |
| $(CF_3SO_2)_2NH$ | 2.2 mole % | 45° C. | 6 h | 0.0 | 88.3 |
| $(CF_3SO_2)_2NH$ | 1.1 mole % | 70° C. | 2.5 h | 3.7 | 85.0 |
| $(C_2F_5SO_2)_2NH$ | 1.1 mole % | 45° C. | 8.5 h | 0.4 | 88.0 |
| $(SO_2CF_2CF_2CF_2SO_2)NH$ | 1.1 mole % | 45° C.* | 6.5 h | 6.1 | 83.9 |
| $(SO_2CF_2CF_2CF_2SO_2)NH$ | 1.1 mole % | 45° C. | 7.5 h | 0.0 | 88.2 |
| $(CF_3SO_2)_3CH$ | 1.1 mole % | 45° C.* | 6 h | 7.7 | 82.5 |
| $Ni((CF_3SO_2)_3C)_2$ | 1.1 mole % | 45° C. | 24.5 h | 5.3 | 83.9 |

*cooling to 0–10° C. during KIP addition
KIP: ketoisophorone
TMHQ-DA: 2,3,5-trimethylhydroquinone diacetate
GC-area %: area percent according to gas chromatography

The invention claimed is:

1. A process for the manufacture of a 2,3,5-trimethylhydroquinone diacylate comprising reacting ketoisophorone with an acylating agent in the presence of a NH- or CH-acidic catalyst.

2. A process according to claim 1, wherein the NH-acidic catalyst is a compound of the general formula

$$[(R^1SO_2)_2N]_xR^2 \quad (I)$$

and the CH-acidic catalyst is a compound of the general formula

$$[(R^3SO_2)_3C]_xR^2 \quad (II)$$

wherein each of $R^1$, independently, signifies a perfluoroalkyl group $C_nF_{2n+1}$ or pentafluorophenyl, or both symbols $R^1$ together signify a poly-difluoromethylene group —$(CF_2)_m$—, $R^2$ signifies a proton or a metal cation selected from the group consisting of boron, magnesium, aluminium, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum and gold cations, each of $R^3$, independently, signifies a perfluoroalkyl group $C_nF_{2n+1}$, m signifies an integer from 2 to 4, n signifies an integer from 1 to 10 and x signifies an integer from 1 to 5, corresponding to the valency of the proton (1) or the metal cation (1, 2, 3, 4, or 5) signified by $R^2$.

3. A process according to claim 2, wherein the catalyst is an NH-acidic catalyst of the general formula I and each of $R^1$ therein signifies trifluoromethyl or pentafluoroethyl, or both symbols $R^1$ therein together signify perfluoro-1,3-propylene.

4. A process according to claim 2, wherein $R^2$ in the NH-acidic catalyst of the general formula I signifies a proton.

5. A process according to claim 2, wherein the catalyst is a CH-acidic catalyst of the general formula II and each of $R^3$ therein signifies trifluoromethyl.

6. A process according to claim 2, wherein $R^2$ in the CH-acidic catalyst of the general formula II signifies a proton or a divalent nickel cation.

7. A process according claim 1, wherein the acylating agent is an acid anhydride, an acyl halide or an enol ester.

8. A process according to claim 7, wherein the acylating agent is a straight or branched chain alkanoic acid anhydride, a straight or branched chain alkanoyl chloride, or, an enol ester.

9. A process according claim 1, wherein the ratio of acylating agent (equivalents) to ketoisophorone (moles) is from about 1:1 to about 5:1.

10. A process according to claim 2, wherein the amount of catalyst of the general formula I or II used is about 0.1 to about 2.0 mole %, based on the moles of ketoisophorone present.

11. A process according to claim 1, wherein the acylating reaction is carried out in the presence of a solvent which is an inert polar or non-polar organic solvent or any mixture of two or more of such solvents.

12. A process according to claim 11, wherein the polar organic solvent is an aliphatic or cyclic ketone or an aliphatic or cyclic ester, and the non-polar organic solvent is an aliphatic or aromatic hydrocarbon.

13. A process according to claim 1, wherein the acylating reaction is carried out at temperatures from about 20° C. to about 60° C.

14. A process according to claim 8, wherein the acylating agent is selected from the group consisting of acetic anhydride, propionic anhydride, butyric anhydride, acetyl chloride, propionyl chloride, butyryl chloride, isopropenyl acetate and isopropenyl butyrate.

15. A process according claim 9, wherein the ratio of acylating agent (equivalents) to ketoisophorone (moles) is from about 2:1 to about 3:1.

16. A process according claim 15, wherein the ratio of acylating agent (equivalents) to ketoisophorone (moles) is about 3:1.

17. A process according to claim 10, wherein the amount of catalyst of the general formula I or II used is about 0.5 to about 1.5 mole %, based on the moles of ketoisophorone present.

18. A process according to claim 17, wherein the amount of catalyst of the general formula I or II used is about 0.8 to about 1.2 mole %, based on the moles of ketoisophorone present.

19. A process according to claim 12, wherein the polar organic solvent is selected from the group consisting of diethyl ketone, isobutyl methyl ketone, cyclopentanone, isophorone, ethyl acetate, isopropyl acetate, γ-butyrolactone, ethylene carbonate and proplyene carbonate, and the non-polar organic solvent is selected from the group consisting of hexane, heptane, octane, benzene, toluene and xylene.

20. A process according to claim 13, wherein the acylating reaction is carried out at temperatures from about 30° C. to about 50° C.

* * * * *